United States Patent [19]

Campbell

[11] Patent Number: 4,490,145
[45] Date of Patent: Dec. 25, 1984

[54] OSTOMY POUCH WITH DEODORIZING FILTER

[75] Inventor: Randolph E. Campbell, Red Bank, N.J.

[73] Assignee: E. R. Squibb & Sons, Inc., Princeton, N.J.

[21] Appl. No.: 507,880

[22] Filed: Jun. 27, 1983

[51] Int. Cl.³ .............................................. A61F 5/44
[52] U.S. Cl. .................................................. 604/333
[58] Field of Search ............... 604/333, 332, 334, 336, 604/337

[56] References Cited

U.S. PATENT DOCUMENTS

| | | | |
|---|---|---|---|
| 3,055,368 | 9/1962 | Baxter | 604/333 |
| 3,121,021 | 2/1964 | Copeland | 117/122 |
| 3,339,546 | 9/1967 | Chen | 604/333 |
| 3,439,677 | 4/1969 | Bonfils | 604/333 |
| 3,690,320 | 10/1970 | Riely | 604/333 |
| 3,759,260 | 9/1973 | Nolan et al. | 604/333 |
| 3,804,091 | 4/1974 | Nolan et al. | 604/333 |
| 3,902,496 | 9/1975 | Eakin | 604/333 |
| 3,952,727 | 4/1976 | Nolan | 604/333 |
| 4,120,715 | 10/1978 | Ockwell et al. | 604/333 |
| 4,185,630 | 1/1980 | Neumeier et al. | 604/333 |
| 4,192,785 | 5/1980 | Chen et al. | 604/333 |
| 4,203,445 | 5/1980 | Jessup et al. | 604/333 |
| 4,211,224 | 7/1980 | Kubach et al. | 604/333 |
| 4,268,286 | 5/1981 | Steer et al. | 55/278 |
| 4,274,848 | 6/1981 | LaGro | 55/387 |
| 4,318,406 | 3/1982 | McLeod | 604/333 |
| 4,331,148 | 5/1982 | Steer et al. | 604/333 |
| 4,367,742 | 1/1983 | Ornstein | 604/333 |
| 4,372,308 | 2/1983 | Steer et al. | 604/333 |
| 4,411,659 | 10/1983 | Jensen et al. | 604/333 X |
| 4,449,970 | 5/1984 | Bevan et al. | 604/333 |

FOREIGN PATENT DOCUMENTS

| | | |
|---|---|---|
| 63898 | 11/1982 | European Pat. Off. . |
| 1541565 | 3/1979 | United Kingdom . |
| 1550960 | 8/1979 | United Kingdom . |
| 2031282 | 4/1980 | United Kingdom . |
| 1571382 | 7/1980 | United Kingdom . |
| 1571657 | 7/1980 | United Kingdom . |
| 2083760 | 3/1982 | United Kingdom . |

Primary Examiner—William H. Grieb
Attorney, Agent, or Firm—Lawrence S. Levinson; Stephen B. Davis

[57] ABSTRACT

An ostomy pouch having a filter element affixed to the outer pouch wall. The outer pouch wall has an aperture and the filter element includes a polymeric film cover and an insert of gas deodorizing material. The film cover also has an aperture and opposite ends of the insert overlie the two apertures.

16 Claims, 5 Drawing Figures

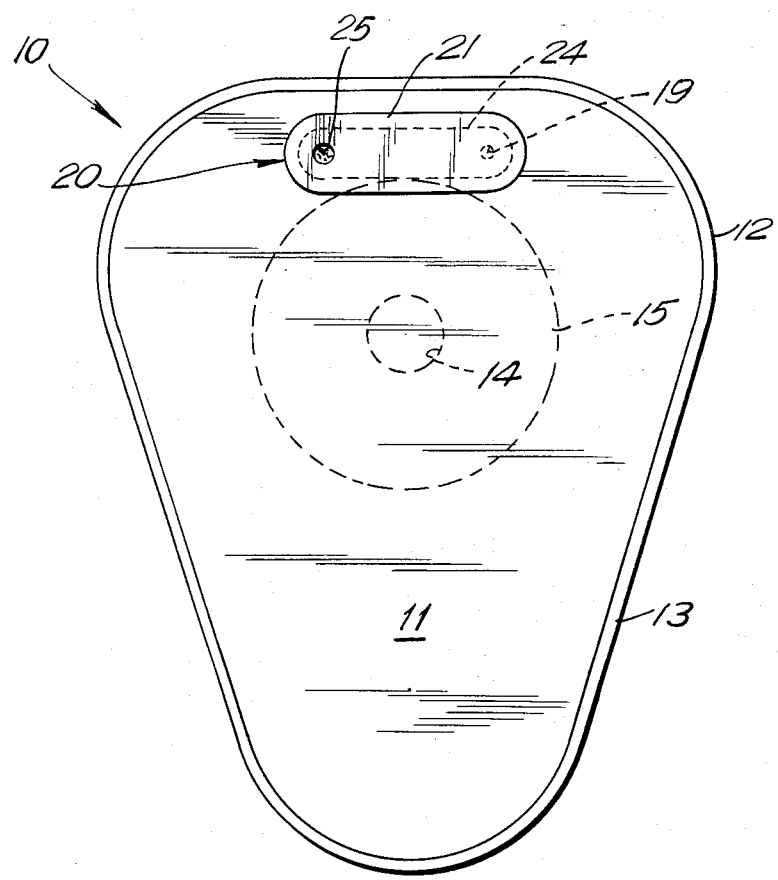
FIG.1
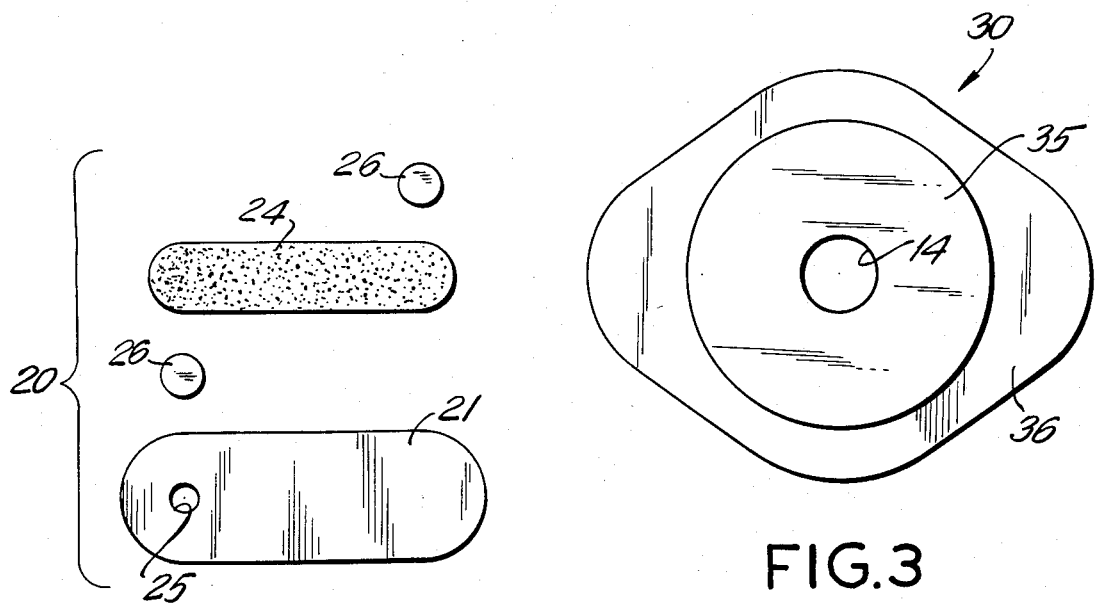
FIG.2
FIG.3

OSTOMY POUCH WITH DEODORIZING FILTER

BACKGROUND OF THE INVENTION

Most ostomates employ some type of bag or pouch system to collect bodily wastes discharged from their surgically created stoma. Today, such pouches are generally formed of light weight, odor proof, flexible polymeric materials and the collection systems are designed to be inconspicuous and permit the ostomate to engage in normal physical activity. However, many ostomates, particularly immediately following surgery, have fears concerning their ability to resume a "normal life". These fears center around worries that the collection system will leak or that odor will escape and that the system will be noticeable even through their outer clothing. Part of these problems are due to the discharge of flatus into the pouch which can cause an embarrassing distention of the pouch.

In order to overcome the problem of gas build up within the pouch, it has been suggested that the pouch be provided with a tortuous path vent opening as note, for example, Baxter in U.S. Pat. No. 3,055,368 and Neumeier et al. in U.S. Pat. No. 4,185,630. Ornstein in U.S. Pat. No. 4,367,742 and Briggs et al. in U.K. Pat. application No. 2,031,282, for example, employ a tortuous path and a deodorizing filter. Other proposals have involved filters which could be attached to the pouch as note, for example, Steer et al. in U.S. Pat. No. 3,268,286 or filters attached over a vent opening in the pouch wall as note, for example, Bevan et al. U.K. Pat. application No. 2,083,760. It has also been suggested to employ a pouch having a deodorizing vent opening in its upper edge as note, for example, Steer et al. in U.S. Pat. No. 4,372,308, Kulbach et al. in U.S. Pat. No. 4,211,224, and Jensen in British Pat. No. 1,541,565. Bonfils in U.S. Pat. No. 3,439,677 disclose a pouch having a vent opening in the outer pouch wall opposite and above the stomal aperture covered by a deodorizing filter. Ockwell et al. in U.S. Pat. No. 4,120,715 and McLeod in U.S. Pat. No. 4,318,406 disclose multi-layered filters adapted to be sealed over a vent opening in the pouch wall. Steer et al. in U.S. Pat. No. 4,331,148 disclose employing a deodorizing cover bag.

Other venting pouch systems are disclosed by Nolan et al. in U.S. Pat. Nos. 3,759,260 and 3,804,091, by Nolan in U.S. Pat. No. 3,952,727, by Jessup et al. in U.S. Pat. No. 4,203,445, by Larsen et al. in British Pat. No. 1,571,382 and by LaGro in U.S. Pat. No. 4,274,848.

SUMMARY OF THE INVENTION

This invention relates to an ostomy pouch having a deodorizing filter element affixed to the outer pouch wall. The filter element consists of a polymeric film cover that is welded or adhesively attached to the outer polymeric pouch wall and an insert of gas deodorizing material located between the polymeric film cover and the polymeric pouch wall. The outer pouch wall and the polymeric film cover are each provided with an aperture. The apertures are not aligned and are covered by opposite ends of the deodorizing material insert. Thus, the build-up of gas pressure within the pouch will cause the gas to travel into the filtering element, through the insert of deodorizing material, and finally be vented to the atmosphere.

The term "ostomy pouch" is used to mean a colostomy or ileostomy or other kind of pouch or bag intended to be worn by a user to receive waste material expelled from a stoma.

BRIEF DESCRIPTION OF THE DRAWINGS

FIG. 1 is a front view of an ostomy pouch including a deodorizing filter element according to this invention;

FIG. 2 is an exploded view showing the elements of a preferred form of the filter element of this invention;

FIG. 3 is a front view of an alternate faceplate for use on the ostomy pouch of this invention;

DETAILED DESCRIPTION OF THE INVENTION

Figure 4:
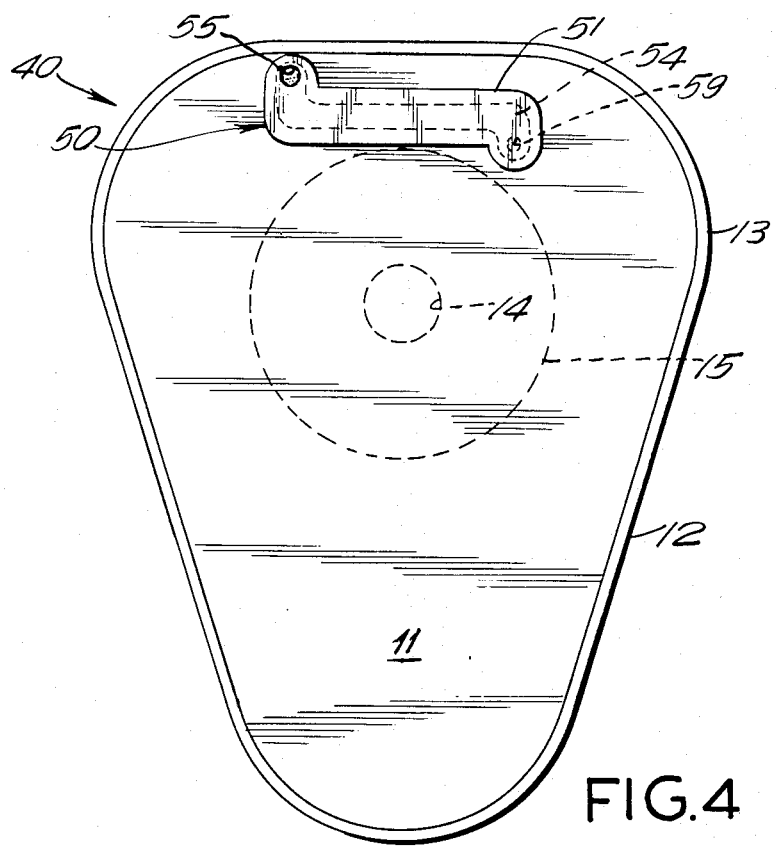
FIG. 4 is a front view of an ostomy pouch employing a filter element of different configuration.

An ostomy pouch 10 including a deodorizing filter element 20 according to this invention is shown in FIG. 1. The pouch 10 consists of body side pouch wall 12 and outer pouch wall 11 sealed together along their peripheral edge 13. The term "body side" refers to that portion of the pouch which in use is closest to the body of the user and outer pouch wall refers to that portion of the pouch furthest from the body of the user.

Body side 12 includes an aperture 14 which can be enlarged so as to fit snugly around the stoma of the user. The stomal aperture is encircled by means for supporting the pouch on the body of the user. Conventionally, this support means is a faceplate 15 which consists of a pressure sensitive medical grade adhesive material having a backing layer that is welded directly to the pouch wall 12.

The medical grade pressure sensitive adhesive can be a microporous acrylic type such as that taught by Copeland in U.S. Pat. No. 3,121,021 or a hydrocolloid containing microporous adhesive as taught by Cilento et al. in European Pat. Application No. 63,898 published on Nov. 3, 1982. The backing layer can be a breathable non-woven material such as one of the commercially available spun-bonded polyester products.

Alternatively, the faceplate 15 may consist of a non-porous pressure sensitive adhesive layer and a polymeric backing film. A particularly suitable adhesive faceplate of this type is taught by Chen in U.S. Pat. No. 3,339,546 and consists of an elastomeric substance such as polyisobutylene and one or more water soluble or swellable hydrocolloids such as the mixture of pectin, gelatin, and sodium carboxymethylcellulose having an impervious polymeric film secured to one surface. This polymeric film can be welded directly to pouch wall 12. Other suitable adhesive faceplates of this type are taught by Chen et al. in U.S. Pat. No. 4,192,785 and by Pawelchak et al. in U.S. application Ser. No. 334,284 filed Dec. 24, 1981.

Alternatively, adhesive faceplate 15 can be replaced by mechanical means for attachment of the pouch to the user. A suitable system is disclosed by Steer et al. in British Pat. No. 1,571,657. Thus, the channel shaped coupling member of Steer et al. could be secured to body side pouch wall 12 around aperture 14.

Pouch 10 has a deodorizing filter element 20 affixed to the outside of outer pouch wall 11. As shown in FIG. 1, the filter element 20 consists of a polymeric film cover 21 that can be welded or adhesively attached to the outside of outer pouch wall 11 and an insert 24 of gas deodorizing material. Outer pouch wall 11 includes an aperture 19 that provides entry into the deodorizing filter element 20 and film cover 21 includes an aperture 25 for venting of the deodorized gas to the atmosphere. Thus, gas built-up within the confines of pouch 10 is continuously being deodorized and vented. Of course, if desired, aperture 25 can be covered with a piece of gas impermeable adhesive tape if one does not wish the venting to occur on a continuous basis.

Preferably, aperture 19 in outer pouch wall 11 is located above stomal aperture 14 in body side pouch wall 12. This reduces the possibility that fecal material discharged from the stoma will contact deodorizing insert 24.

Pouch walls 11 and 12 are selected from polymeric materials and laminates which possess the properties of being moisture impermeable, odor impermeable, and capable of being heat sealed or impulse welded. Suitable materials include polyethylene, a copolymer of vinyl chloride and polyvinylidene chloride, etc., and laminates thereof such as a laminate of ethylene vinylacetate or polyethylene and a copolymer of vinyl chloride and polyvinylidene chloride and a triple laminate composed of an outer and inner layer of ethylene vinylacetate and a core of a copolymer of vinyl chloride and polyvinylidene chloride. Pouch walls 11 and 12 will be from about 2 to about 4 mils thick. The same materials are suitable for use as polymeric film cover 21. Polymeric film cover 21 can be welded to outer pouch wall 11 by heat welding or other techniques if the polymeric materials are compatible or the inner surface of cover 21 can be coated with a pressure sensitive acrylic type adhesive.

FIG. 2 shows an alternative construction for filter element 20. According to this embodiment, barrier layers 26 are provided on both sides of the insert 24 of gas deodorizing material to cover apertures 25 and 19. The barrier layers are formed of gas permeable, liquid impermeable materials. They function to keep the gas deodorizing material dry and control the rate at which gas can pass from the pouch into the filtering element and then be vented from the filtering element into the atmosphere. Thus, gas pressure in the interior of the pouch will not fall suddenly to such a level that the outer and body side pouch walls collapse into contact with each other. If this occurs, the user may suffer pain or discomfort as the outer pouch wall contacts the sensitive end of the stoma, and free discharge of material from the stoma may be hindered. At the same time, the porosity of the layers are chosen so that the obstruction to escaping gases offered by the layers are not so great as to prevent adequate venting of flatus gases from the pouch interior.

Of course, the filtering element shown in FIG. 2 can be modified so as to include only one barrier layer which would cover either aperture 19 or aperture 25. The surface of barrier layer 26 contacting insert 24 is coated with pressure sensitive adhesive to facilitate assembly of the filtering element.

FIG. 3 shows an alternative adhesive faceplate 30 which can be employed with the ostomy pouch of this invention. This faceplate consists of a layer of non-porous hydrocolloid containing adhesive 35 of from about 10 to about 30 mils thickness attached to a tape 36 of about 2 to 3 mils thickness. Tape 36 consists of a microporous adhesive and a breathable non-woven backing. The tape 36 extends beyond the borders of adhesive layer 35 and only portions of the backing beneath the area of adhesive layer 35 are welded to pouch wall 12 so that tape 36 is more able to follow the contours of the body. Of course, the exposed adhesive surfaces of faceplates 15 and 30 are covered with silicone coated release paper until the pouch is applied to the body.

FIG. 4 shows an ostomy pouch 40 identical to that of FIG. 1 except that filter element 50 consists of polymeric film cover 51 and deodorizing gas insert 54 both of an elongated shape with protrusions at both ends. Aperture 59 in outer pouch wall 11 provides entry for the gas into the filter element and aperture 55 in film cover 51 provides for the venting of the gas from the filter element to the atmosphere. Of course, barrier layers 26 can be provided over one or both of the apertures as explained above. The configuration of the insert shown in FIG. 4 will result in a longer path through which the gas must travel before venting. Of course, it is possible to further increase the path by employing a filter element consisting of a film cover and deodorizing insert of serpentine configuration.

Figure 5:
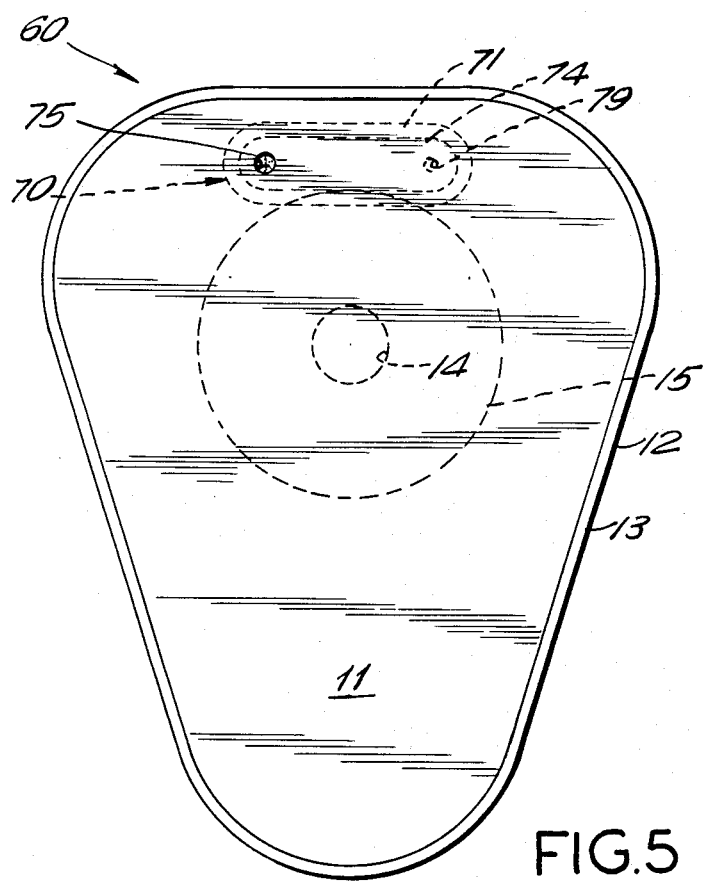
FIG. 5 is a front view of an ostomy pouch including a deodorizing filter element located on the inside of the outer pouch wall.

FIG. 5 shows a alternate embodiment of this invention wherein pouch 60 includes filter element 70 affixed to the inside of outer pouch wall 11. Filter element 70 consists of a polymeric film cover 71 that can be welded or adhesively attached to the inside of outer pouch wall 11 and an insert 74 of gas deodorizing material. Film cover 71 includes an aperture 79 that provides entry into the deodorizing filter element 70 and outer pouch wall 11 includes an aperture 75 for venting of the deodorized gas to the atmosphere. Thus, gas built-up within the confines of pouch 60 is continuously being deodorized and vented. Barrier layers 26 can be included to cover both or only one of apertures 75 and 79 as explained above.

The gas deodorizing inserts 24, 54 and 74 preferably contain activated carbon as the gas adsorbing and deodorizing agent. One type of suitable material is a sheet of foamed open-cell non-woven synthetic polymeric material, for example, polyurethane, having a large number of activated carbon particles distributed over one of its major surfaces. Such a material is commercially available under the tradename Bondina. Another type of suitable deodorizing material is a felt pad impregnated with activated carbon in fine particulate form. Various types of such carbon cloth are commercially available.

Preferably, the insert is made by cutting the shape from a sheet of filter medium known as "Bondina" activated carbon filter No. S.442.

The barrier layer 26 can be made from a microporous adhesive tape such as that taught by Copeland in U.S. Pat. No. 3,121,021 or that commercially available as "Bondina" non-woven viscous medical tape, No. T.1562 F.

The ostomy pouches of this invention are assembled by forming pouch walls 11 and 12 in the desired configuration. The stomal aperture is punched out of wall 12, a small aperture is punched in wall 11, and an attaching means is affixed around the stomal aperture. The filter element with none, one, or two barrier layers is assembled and welded or adhesively attached to the outside or inside surface (when pouch is assembled) of outer pouch wall 11. Finally, pouch walls 11 and 12 are sealed together along their peripheral edge 13.

The ostomy pouches 10, 40, and 60 are shown as being of a pear shape configuration decreasing in width from top to bottom. While this shape is preferred, other shapes such as elliptical could be employed.

In order to increase the capacity of the pouch, the outer pouch wall can be provided with one or more pleats extending from the top to the bottom edge such as those shown by Eakin in U.S. Pat. No. 3,902,496. Also, while the pouches 10, 40, and 60 are shown as being of the closed, disposable type, the filter element of this invention could be employed with a drainable pouch. In this case, pouch walls 11 and 12 would each have a narrow tail portion and the peripheral seal 13 would not extend across the bottom opening. A clip or other means would be provided to seal off the bottom opening.

In order to improve the feel of the pouch against the body, a layer of open-mesh flocked polymeric material can be employed outside body side wall 12. A suitable material for this purpose is a perforated low density polyethylene such as that available under the tradename Vispore from Ethyl Visqueen Corp. This material would be of the same configuration as pouch walls 11 and 12 and would be sealed to the pouch walls at the peripheral edge 13.

What is claimed is:

1. An ostomy pouch comprising two pouch walls of moisture proof, odor proof polymeric materials sealed together along at least a substantial portion of their peripheral edge to form said pouch, one of said pouch walls having an aperture adapted in use to fit around the stoma of the user, said stomal aperture encircled by means for attaching said pouch to the body of the user, the second pouch wall having an aperture in its upper region above the stomal opening in the first pouch wall so that fecal matter discharged from the stoma into the pouch will not readily contact said second pouch wall aperture, a filter element comprising a polymeric film cover having an aperture and an insert of gas deodorizing material, and said film cover affixed to said second pouch wall so that opposite ends of said insert of gas deodorizing material overlie said second pouch wall and said film cover apertures whereby gas within the pouch travels into said filter element and through said gas deodorizing material before being vented to the atmosphere.

2. Am ostomy pouch according to claim 1 wherein said polymeric film cover of said filter element is affixed to the surface of said second pouch wall which becomes the outside of said pouch when the two pouch walls are sealed together along their peripheral edge.

3. An ostomy pouch according to claim 2 wherein said filter element includes a barrier layer of water impermeable, gas permeable material and said barrier layer is positioned between said second pouch wall aperture and said insert of gas deodorizing material.

4. An ostomy pouch according to claim 2 wherein said filter element includes a barrier layer of water impermeable, gas permeable material and said barrier layer is positioned between said film cover aperture and said insert of gas deodorizing material.

5. An ostomy pouch according to claim 2 wherein said filter element includes two barrier layers of water impermeable, gas permeable material, one of said barrier layers is positioned between said second pouch wall aperture and said insert of gas deodorizing material and the other barrier layer is positioned between said film cover aperture and said insert of gas deodorizing material.

6. an ostomy pouch according to claim 1 wherein said polymeric film cover of said filter element is affixed to the surface of said second pouch wall which becomes the inside of said pouch when the two pouch walls are sealed together along their peripheral edge.

7. An ostomy pouch according to claim 6 wherein said filter element includes a barrier layer of water impermeable, gas permeable material and said barrier layer is positioned between said second pouch wall aperture and said insert of gas deodorizing material.

8. An ostomy pouch according to claim 6 wherein said filter element includes a barrier layer of water impermeable, gas permeable material and said barrier layer is positioned between said film cover aperture and said insert of gas deodorizing material.

9. An ostomy pouch according to claim 6 wherein said filter element includes two barrier layers of water impermeable, gas permeable material, one of said barrier layers is positioned between said second pouch wall aperture and said insert of gas deodorizing material and the other barrier layer is positioned between said film cover aperture and said insert of gas deodorizing material.

10. An ostomy pouch according to claim 1 wherein said insert of deodorizing material contains activated carbon.

11. An ostomy pouch according to claim 10 wherein said insert of deodorizing material is a foamed open-cell polyurethane foam having activated carbon particles distributed over one surface.

12. An ostomy pouch according to claim 1 wherein said two pouch walls are sealed together along their entire peripheral edge.

13. An ostomy pouch according to claim 1 wherein said polymeric film cover has a coating of pressure sensitive adhesive on one side and is affixed to said second pouch wall by means of said adhesive.

14. An ostomy pouch according to claim 1 wherein said polymeric film cover is welded to said second pouch wall.

15. An ostomy pouch according to claim 1 wherein said means for attaching said pouch to the body of the user is an adhesive faceplate consisting of an adhesive layer and a backing which is welded to said pouch wall around said stomal aperture.

16. An ostomy pouch according to claim 15 wherein said adhesive faceplate consists of a microporous adhesive layer and a non-woven breathable backing layer that is welded to said pouch wall around said stomal aperture.

* * * * *